United States Patent

Yanagisawa et al.

[11] Patent Number: 5,231,207
[45] Date of Patent: Jul. 27, 1993

[54] ORGANOSILICON COMPOUND

[75] Inventors: Hideyoshi Yanagisawa; Masaaki Yamaya; Masayuki Takahashi; Takanori Katou, all of Gunma, Japan

[73] Assignee: Shin-Etsu Chemical Co., Ltd., Tokyo, Japan

[21] Appl. No.: 960,626

[22] Filed: Oct. 14, 1992

[30] Foreign Application Priority Data

Oct. 15, 1991 [JP] Japan .................... 3-295125

[51] Int. Cl.$^5$ ................................ C07F 7/10
[52] U.S. Cl. ..................................... 556/424
[58] Field of Search ......................... 556/424

[56] References Cited

U.S. PATENT DOCUMENTS

| | | | |
|---|---|---|---|
| 3,249,535 | 5/1966 | Keil | 556/424 X |
| 3,627,800 | 12/1971 | Owen et al. | 556/424 |
| 4,472,566 | 9/1987 | Ziernelis et al. | 556/424 X |
| 4,493,926 | 1/1985 | Williams et al. | 556/424 X |
| 4,670,423 | 6/1987 | Böshagen et al. | 556/424 X |
| 4,806,667 | 2/1989 | Böshagen et al. | 556/424 |
| 5,077,420 | 12/1991 | Emanie et al. | 556/424 X |

Primary Examiner—Paul F. Shaver
Attorney, Agent, or Firm—Millen, White, Zelano & Branigan

[57] ABSTRACT

Disclosed in a novel organosilane compound represented by the general formula $$(R^1O)_m Me_{3-m}Si-R^2-NH-R^3-NH_2,$$

in which Me is a methyl group, $R^1$ is a methyl or ethyl group, $R^2$ is a divalent hydrocarbon group having 1 to 10 carbon atoms, $R^3$ is a divalent hydrocarbon group having 7 to 10 carbon atoms of which six carbon atoms jointly form a benzene ring, at least one of the nitrogen atoms in the amino and imino groups being not directly bonded to the carbon atom which is a member of the benzene ring, and the subscript m is 1,2 or 3.

4 Claims, 2 Drawing Sheets

ORGANOSILICON COMPOUND

BACKGROUND OF THE INVENTION

The present invention relates to a novel organosilicon compound or, more particularly, to an organosilane compound having an amino group and an alkoxy group in the molecule and useful as a coupling agent between inorganic and organic materials. The silane compound is not described in any prior art literatures.

It is an established technology that the compatibility between an inorganic material and an organic material is improved by using an organosilane compound having an amino group and an alkoxy group in the molecule. Such an organosilane compound is used, for example, as an adhesion aid in an adhesive composition for adhesive bonding of an inorganic material and an organic material, additive in inorganic-organic composite materials, surface-modification of inorganic materials and so on. Such an organo-silane compound is useful also as an intermediate in the synthesis of various kinds of organosilicon compounds.

Examples of the organosilane compounds of the above mentioned type include 3-aminopropyl trimethoxy silane, 3-aminopropyl triethoxy silane, 3-aminopropyl methyl diethoxy silane. N-2-aminoethyl-3-aminopropyl methyl dimethoxy silane and the like as an amino-substituted-alkyl alkoxy silane compound as well as N-benzyl-3-aminopropyl trimethoxy silane, N-phenyl-3-aminopropyl trimethoxy silane, 2-(N-2-aminoethyl aminomethyl)phenylethyl trimethoxy silane and the like as an aryl group-containing organosilane compound of the type.

These organosilane compound having an amino group and an alkoxy group in the molecule are of course effective in the above mentioned applications as a coupling agent between an inorganic material and an organic material. A problem in these known compounds is that the thermal stability thereof is relatively low so that the compound is sometimes colored in yellow or brown when the compound is exposed to air at an elevated temperature. Accordingly, the material treated therewith or composition admixed therewith is also unstable at an elevated temperature along with the relatively low resistance against moisture.

SUMMARY OF THE INVENTION

The present invention accordingly has an object to provide an organosilane compound which has an amino group and an alkoxy group in the molecule and is still free from the above mentioned problems and disadvantages in the prior art organosilane compounds of such a type.

Thus, the organosilane compound having an amino group and an alkoxy group in the molecule provided by the present invention is a compound represented by the general formula $$(R^1O)_m Me_{3-m}Si-R^2-NH-R^3-NH_2, \quad (I)$$

in which Me is a methyl group, $R^1$ is a methyl or ethyl group, $R^2$ is a divalent hydrocarbon group having 1 to 10 carbon atoms, $R^3$ is a divalent hydrocarbon group having 7 to 10 carbon atoms of which six carbon atoms jointly form a benzene ring, at least one of the nitrogen atoms in the amino and imino groups being not directly bonded to the carbon atom which is a member of the benzene ring, and the subscript m is 1, 2 or 3.

DETAILED DESCRIPTION OF THE PREFERRED EMBODIMENTS

Figure 1:
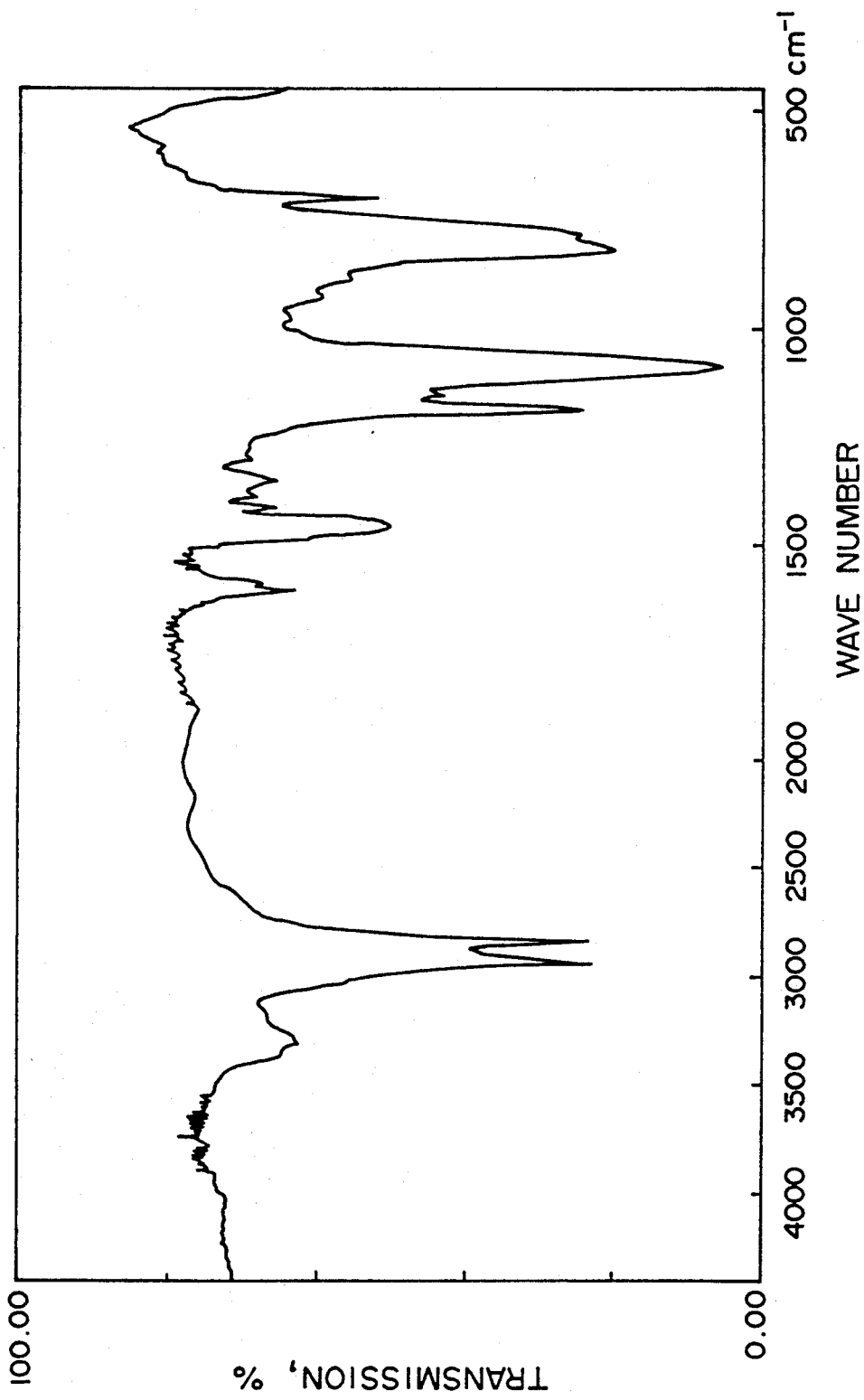
FIG. 1 shows an infrared absorption spectrum of the organosilane compound prepared in Example 1.

Thus, the organosilicon compound of the present invention discovered and newly synthesized by the inventors is an organosilane compound represented by the general formula $$(R^1O)_m Me_{3-m}Si-R^2-NH-R^3-NH_2, \quad (I)$$

in which Me is a methyl group, $R^1$ is a methyl or ethyl group, $R^2$ is a divalent hydrocarbon group having 1 to 10 carbon atoms, $R^3$ is a divalent hydrocarbon group having 7 to 10 carbon atoms of which six carbon atoms jointly form a benzene ring and the subscript m is 1, 2 or 3. It is essential that either one or both of the nitrogen atoms in the amino and imino groups are not directly bonded to the carbon atoms forming the benzene ring.

Examples of the divalent hydrocarbon group denoted by $R^2$ in the formula include those expressed by the following formulas, of which the carbon atom at the left-hand end is bonded to the silicon atom and that at the right-hand end is bonded to the nitrogen atom of the imino group —NH—: —$CH_2$—; —$(CH_2)_2$—; —CHMe—; —$(CH_2)_3$—; —$CHMeCH_2$—; —$CH_2CHMe$—; —$CMe_2$—; —$(CH_2)_4$—; —$CHMe$—$(CH_2)_2$—; —$CH_2CHMeCH_2$—; —$(CH_2)_5$—; —$(CH_2)_6$—; —$(CH_2)_7$—; —$(CH_2)_8$—; —$(CH_2)_9$—; —$(CH_2)_{10}$—; —CHMe—$(CH_2)_4$—; —CHMe—$(CH_2)_8$—; —$(CH_2)_2$—Pn—$CH_2$—and the like, in which Me is a methyl group and Pn is a phenylene group.

The group denoted by $R^3$ in the general formula (I) is a divalent hydrocarbon group having 7 to 10 carbon atoms, of which six carbon atoms jointly form a benzene ring. Examples of the divalent hydrocarbon group denoted by $R^3$ in the formula include those expressed by the following formulas, in which Pn is a 1,2-, 1,3- or 1,4-phenylene group, and the carbon atom at the left-hand end or one of the carbon atoms in the phenylene group, when it is at the left-hand end, is bonded to the nitrogen atom of the imino group —NH— while the carbon atom at the right-hand end or one of the carbon atoms in the phenylene group, when it is at the right-hand end, is bonded to the nitrogen atom of the amino group —$NH_2$: —$CH_2$—Pn—; —$CH_2$—Pn—$CH_2$—; —$CH_2$—Pn—$(CH_2)_2$—; —$CH_2$—Pn—$(CH_2)_3$—; —$(CH_2)_2$—Pn—; —$(CH_2)_2$—Pn—$CH_2$—; —$(CH_2)_2$—Pn—$(CH_2)_2$—; —$(CH_2)_3$—Pn—; —$(CH_2)_3$—Pn—$CH_2$—; and the like.

Examples of the inventive organosilicon compounds represented by the above given general formula (I) include those expressed by the following structural formulas, in which Me is a methyl group, Et is an ethyl group and Pn is a 1,2-, 1,3- or 1,4-phenylene group:

$(MeO)_3Si$—$(CH_2)_3$—NH—$CH_2$—Pn—$CH_2NH_2$;
$(MeO)_3Si$—$(CH_2)_3$—NH—Pn—$CH_2NH_2$;
$(MeO)_3Si$—$(CH_2)_3$—NH—Pn—$(CH_2)_2NH_2$;
$(MeO)_3Si$—$(CH_2)_3$—NH—$CH_2$—Pn—$NH_2$;
$(MeO)_3Si$—$(CH_2)_3$—NH—$(CH_2)_2$—Pn—$NH_2$;
$(MeO)_3Si$—$(CH_2)_3$—NH—$(CH_2)_2$—Pn—$(CH_2)_2NH_2$;

(MeO)₃Si—(CH₂)₃—NH—(CH₂)₂—Pn—CH₂NH₂;
(MeO)₃Si—(CH₂)₃—NH—CH₂—Pn—(CH₂)₂NH₂;
(MeO)₃Si—CH₂—NH—CH₂—Pn—CH₂NH₂;
(MeO)₃Si—CH₂—CHMe—CH₂—NH—CH₂—P-
  n—CH₂NH₂;
(MeO)₂MeSi—(CH₂)₃—NH—CH₂—Pn—CH₂NH₂;
(MeO)Me₂Si—(CH₂)₃—NH—CH₂—Pn—CH₂NH₂;
(EtO)₃Si—CH₂—NH—CH₂—Pn—CH₂NH₂;
(EtO)₂MeSi—(CH₂)₃—NH—CH₂—Pn—CH₂NH₂;
(MeO)₃Si—(CH₂)₆—NH—CH₂—Pn—CH₂NH₂;
(MeO)₂MeSi—(CH₂)₆—NH—CH₂—Pn—CH₂NH₂;
(EtO)₃Si—(CH₂)₆—NH—CH₂—Pn—CH₂NH₂;
(MeO)₃Si—(CH₂)₁₀—NH—CH₂—Pn—CH₂NH₂;
(MeO)₂MeSi—(CH₂)₁₀—NH—CH₂—Pn—CH₂NH₂;
(EtO)₃Si—(CH₂)₁₀—NH—CH₂—Pn—CH₂NH₂; and
(MeO)₃Si—(CH₂)₂—Pn—CH₂—NH—CH₂—P-
  n—CH₂NH₂.

The organosilicon compound of the present invention can be prepared by the following synthetic method. Namely, a halogenoalkyl alkoxy silane compound represented by the general formula $$(R^1O)_m(CH_3)_{3-m}Si-R^2-X, \quad (II)$$

in which $R^1$, $R^2$ and m have the same meaning as defined above and X is an atom of halogen such as chlorine and bromine, is reacted with a diamine compound represented by the general formula $$H_2N-R^3-NH_2. \quad (III)$$

in which $R^3$ has the same meaning as defined above and at least one of the nitrogen atoms of the two amino groups is not directly bonded to the carbon atom in the benzene ring of the group $R^3$, at a temperature in the range from 50° to 200° C. or, preferably, from 80° to 150° C. for a length of time of 30 minutes to 30 hours. The amount of the diamine compound in the reaction mixture is at least 0.5 mole or, preferably, at least 1.0 mole per mole of the silane compound. The reaction can proceed smoothly in the presence of a hydrogen halide acceptor which is an organic base including tertiary amine compounds such as trimethyl amine, triethyl amine, pyridine and the like as well as urea. It is optional that the diamine compound of the general formula (III) is used in an amount in excess of stoichiometry so that the excessive amount thereof can serve as a hydrogen halide acceptor. Since the hydrogen halide formed by the reaction forms a salt with the amino or imino group in the desired reaction product, it is a usual practice that the salt of the hydrogen halide after completion of the reaction is decomposed by the addition of a strong alkali such as sodium alkoxide to liberate the inventive silane compound.

If necessary, the mixture of the reactants in the above mentioned reaction can be diluted with an organic solvent which is exemplified, though not limitative, by aromatic hydrocarbon solvents such as benzene, toluene and xylene, aliphatic hydrocarbon solvents such as pentane, hexane, nonane, octane and decane, ethers such as diethyl ether, tetrahydrofuran and dioxane, alcohols such as methyl and ethyl alcohols, chlorinated hydrocarbons such as perchloroethane, perchloroethylene, trichloroethane, chloroform and carbon tetrachloride, amide compounds such as N,N-dimethyl formamide, esters such as methyl acetate, ethyl acetate and butyl acetate, and so on.

The above described organosilicon compound of the invention is a novel compound not known in the prior art nor described in any literatures. It is useful as a coupling agent between inorganic and organic materials and serves as an additive of an adhesive composition, modifier in an inorganic-organic composite material, surface-treatment agent of an inorganic material, modifier of an organic resin, polymerization initiator or polymerization stopper in the preparation of n organic polymer, and so on.

The above mentioned inorganic-organic composite materials include those by the combination of an organic resin such as epoxy resins, polyimide resins, polyamide resins, melamine resins, polyester resins, urea resins, polyurethane resins, polyvinyl chloride resins, polyethylene resins, polypropylene resins, polyphenylene oxide resins, polyphenylene sulfide resins, polyether-ether ketone resins, polyacetal resins, polycarbonate resins, polyamino resins, phenolic resins, furan resins and the like and an inorganic filler such as glass powder, mica flakes, aluminum hydroxide, magnesium hydroxide, silica sand, copper powder, iron powder, iron oxide, aluminum powder, aluminum oxide and the like. These inorganic and metallic materials can be imparted with improved surface properties by the treatment with the inventive organosilicon compound.

The novel organosilicon compound of the invention is also useful as an intermediate in the synthesis of various kinds of organosilicon compounds or silicones such as reactive silicone oils, reactive silicone varnishes, silane coupling agents and the like.

When used in the above described applications, the inventive amino-containing organosilane compound can impart the final product with improved thermal stability and resistance against moisture by virtue of the presence of an aromatic structure in the molecule as compared with conventional amino-containing alkoxy silane compounds such as 3-aminopropyl trimethoxy silane and N-2-aminoethyl-3-aminopropyl trimethoxy silane while coloring thereof can be reduced as a result of the fact that at least either one of the nitrogen atoms in the amino and imino groups is not directly bonded to the carbon atom in the benzene ring.

In the following, examples are given to illustrate the procedure for the synthetic preparation of the inventive organosilicon compound and characterization thereof.

EXAMPLE 1

Into a flask of 1 liter capacity equipped with a stirrer, thermometer, reflux condenser and dropping funnel were introduced 408.0 g (3.0 moles) of 1,3-xylylene diamine and 200 g of xylene to form a reaction mixture, into which 198.5 g (1.0 mole) of 3-chloropropyl trimethoxy silane were added dropwise under an atmosphere of nitrogen while the reaction mixture in the flask was kept at a temperature of 110° to 120° C. After completion of the dropwise addition of the silane compound, the reaction mixture was heated at 130° C. for 10 hours under continuous agitation.

Thereafter, 183.2 g of a 28% methyl alcohol solution containing 0.95 mole of sodium methoxide were added dropwise into the reaction mixture kept at 60° C. followed by further continued agitation for 1 hour at the same temperature. After cooling to room temperature, the reaction mixture was filtered to remove the precipitates of sodium chloride as the by-product. The filtrate was stripped of the solvent and other volatile matters by distillation at 150° C. under a pressure of 3 mmHg to give 238.4 g of a clear and yellow liquid as a product.

Figure 2:
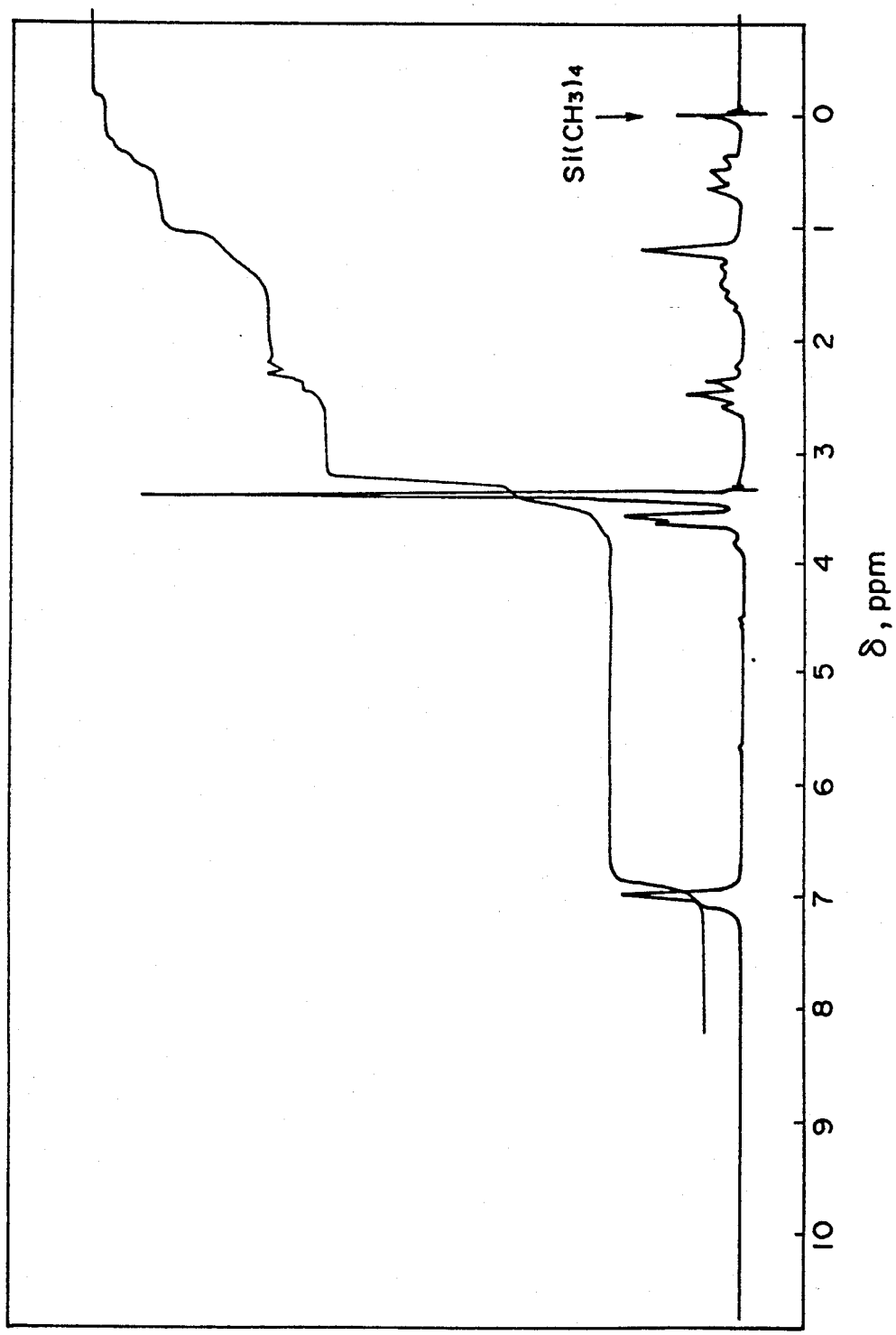
FIG. 2 shows a $^1$H-nuclear magnetic resonance absorption spectrum of the organosilane compound prepared in Example 1.

The thus obtained product was subjected to the elementary analysis, infrared absorption spectrophotometry and $^1$H-nuclear magnetic resonance spectrometry with tetramethyl silane as the internal standard ($\delta=0.00$ ppm) to give the results from which the product compound could be identified to be N-[(3-aminomethylphenyl)methyl]-3-aminopropyl trimethoxy silane. The spectra obtained in the infrared absorption spectrophotometry and the NMR spectrometry are shown in FIGS. 1 and 2, respectively. The above mentioned yield of the product corresponds to 83.2% of the theoretical value. The product had an amine equivalent of 152 g/mole, which is in good coincidence with the theoretical value of 149 g/mole, by the neutralization titration with hydrochloric acid.

Following are the results of the elementary analysis.

|  | C | H | Si | N |
|---|---|---|---|---|
| Calculated, %, for $C_{14}H_{26}O_3N_2Si$ | 56.34 | 8.78 | 9.41 | 9.39 |
| Found, % | 56.41 | 8.68 | 9.29 | 9.52 |

EXAMPLE 2

The experimental procedure was substantially the same as in Example 1 excepting replacement of 198.5 g (1.0 mole) of 3-chloropropyl trimethoxy silane with 138.5 g (1.0 mole) of chloromethyl dimethyl methoxy silane to give 200.6 g of a clear and yellow liquid as the product. This product could be identified from the results of the elementary analysis, infrared absorption spectrophotometry and $^1$H-NMR spectrometry to be N-[(3-aminomethylphenyl)methyl]aminomethyl dimethyl methoxy silane. The amine equivalent of this product was 124 g/mole by the neutralization titration with hydrochloric acid, which was in good coincidence with the theoretical value of 119 g/mole. The above mentioned yield of the product compound corresponds to 84.3% of the theoretical value.

EXAMPLE 3

The experimental procedure was substantially the same as in Example 1 excepting replacement of 408.0 g (3.0 moles) of 1,3-xylylene diamine with 492.0 g (3.0 moles) of 1,4-bis(2-aminoethyl) benzene to give 154.2 g of a clear and yellow liquid as the product. This product could be identified from the results of the elementary analysis, infrared absorption spectrophotometry and $^1$H-NMR spectrometry to be N-[2-(4-aminoethylphenyl)ethyl]-3-aminopropyl trimethoxy silane. The amine equivalent of this product was 166 g/mole by the neutralization titration with hydrochloric acid, which was in good coincidence with the theoretical value of 163 g/mole. The above mentioned yield of the product compound corresponds to 47.3% of the theoretical value.

EXAMPLE 4

The experimental procedure was substantially the same as in Example 1 excepting replacement of 198.5 g (1.0 mole) of 3-chloropropyl trimethoxy silane with 383 g (1.0 mole) of 10-bromodecyl trimethoxy silane to give 336.4 g of a clear and brown liquid as the product. This product could be identified from the results of the elementary analysis, infrared absorption spectrophotometry and $^1$H-NMR spectrometry to be N-[(3-aminomethylphenyl)methyl]-10-aminodecyl triethoxy silane. The amine equivalent of this product was 223 g/mole by the neutralization titration with hydrochloric acid, which was in good coincidence with the theoretical value of 219 g/mole. The above mentioned yield of the product compound corresponds to 76.8% of the theoretical value.

What is claimed is:

1. An organosilicon compound represented by the general formula

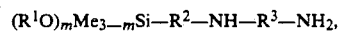

$(R^1O)_mMe_{3-m}Si-R^2-NH-R^3-NH_2$, in which Me is a methyl group, $R^1$ is a methyl or ethyl group, $R^2$ is a divalent hydrocarbon group having 1 to 10 carbon atoms, $R^3$ is a divalent hydrocarbon group having 7 to 10 carbon atoms of which six carbon atoms jointly form a benzene ring, at least one of the nitrogen atoms in the amino and imino groups being not directly bonded to the carbon atom which is a member of the benzene ring, and the subscript m is 1, 2 or 3.

2. The organosilicon compound as claimed in claim 1 in which the group denoted by $R^2$ is selected from the class consisting of the groups expressed by the formulas: $-CH_2-$; $-(CH_2)_2-$; $-CHMe-$; $-(CH_2)_3-$; $-CHMeCH_2$; $-CH_2CHMe-$; $-CMe_2-$; $-(CH_2)_4-$; $-CHMe-(CH_2)_2-$; $-CH_2CHMeCH_2-$; $-(CH_2)_5-$; $-(CH_2)_6-$; $-(CH_2)_7-$; $-(CH_2)_8-$; $-(CH_2)_9-$; $-(CH_2)_{10}-$; $-CHMe-(CH_2)_4-$; $-CHMe-(CH_2)_8-$; and $-(CH_2)_2-Pn-CH_2-$, in which Me is a methyl group and Pn is a phenylene group.

3. The organosilicon compound as claimed in claim 1 in which the group denoted by $R^3$ is selected from the class consisting of the groups expressed by the formulas: $-CH_2-Pn-$; $-CH_2-Pn-CH_2-$; $-CH_2-Pn-(CH_2)_2-$; $-CH_2-Pn-(CH_2)_3-$; $-(CH_2)_2-Pn-$; $-(CH_2)_2-Pn-CH_2-$; $-(CH_2)_2-Pn-(CH_2)_2-$; $-(CH_2)_3-Pn-$; and $-(CH_2)_3-Pn-CH_2-$, in which Pn is a phenylene group, the carbon atom at the left-hand end in the formula or one of the carbon atoms in the phenylene group, when the same is at the left-hand end in the formula, is bonded to the nitrogen atom of the imino group $-NH-$ and the carbon atom at the right-hand end in the formula or one of the carbon atoms in the phenylene group, when the same is at the right-hand end in the formula, is bonded to the nitrogen atom of the amino group $-NH_2$.

4. The organosilicon compound as claimed in claim 1 in which the subscript m is 2 or 3.

* * * * *